United States Patent
Harper et al.

(10) Patent No.: US 10,124,027 B2
(45) Date of Patent: Nov. 13, 2018

(54) THERAPEUTIC BACTERIOPHAGE COMPOSITIONS

(71) Applicant: BioControl Limited, Sharnbrook, Bedfordshire (GB)

(72) Inventors: David Harper, Sharnbrook (GB); Katy Blake, Sharnbrook (GB)

(73) Assignee: BIOCONTROL LIMITED, Sharnbrook (GB)

( * ) Notice: Subject to any disclaimer, the term of this patent is extended or adjusted under 35 U.S.C. 154(b) by 0 days.

(21) Appl. No.: 14/398,384

(22) PCT Filed: May 3, 2013

(86) PCT No.: PCT/GB2013/051163
§ 371 (c)(1),
(2) Date: Oct. 31, 2014

(87) PCT Pub. No.: WO2013/164640
PCT Pub. Date: Nov. 7, 2013

(65) Prior Publication Data
US 2015/0118191 A1  Apr. 30, 2015

(30) Foreign Application Priority Data

May 4, 2012 (GB) .................................. 1207910.9
Oct. 9, 2012 (GB) .................................. 1218083.2

(51) Int. Cl.
*C12N 1/12* (2006.01)
*A61K 35/76* (2015.01)
*A01N 63/00* (2006.01)
*C12Q 1/18* (2006.01)

(52) U.S. Cl.
CPC .............. *A61K 35/76* (2013.01); *A01N 63/00* (2013.01); *C12Q 1/18* (2013.01); *Y02A 50/473* (2018.01)

(58) Field of Classification Search
CPC .................................. A61K 35/76; C12Q 1/18
USPC ........................................................ 435/243
See application file for complete search history.

(56) References Cited

U.S. PATENT DOCUMENTS

| | | | |
|---|---|---|---|
| 8,282,920 B2 | 10/2012 | Heo et al. | |
| 8,685,695 B2 | 4/2014 | Müller | |
| 2006/0094076 A1 | 5/2006 | Stave et al. | |
| 2009/0246336 A1 | 10/2009 | Burnett et al. | |
| 2011/0014157 A1 | 1/2011 | Muller | |

FOREIGN PATENT DOCUMENTS

| | | |
|---|---|---|
| JP | 2006-528166 A | 12/2006 |
| JP | 2010-187661 A | 9/2010 |
| JP | 2011-050373 A | 3/2011 |
| JP | 2011-517557 A | 6/2011 |
| WO | WO 02/086154 | 10/2002 |
| WO | WO 03/080823 | 10/2003 |
| WO | WO 2005/009451 | 2/2005 |
| WO | WO-2005/009451 A1 | 2/2005 |
| WO | WO 2010/06044 | 6/2010 |
| WO | WO 2010/090542 | 8/2010 |
| WO | WO 2013/164640 | 11/2013 |

OTHER PUBLICATIONS

Andreatti Filho et al. "Ability of bacteriophages isolated from different sources to reduce *Salmonella enterica* serovar enterditis in vitro and in vivo". Poultry Science, 2007, 86, pp. 1904-1909.*
Goodridge et al. "Designing Phage Therapeutics". Current Pharmaceutical Biotechnology, 2010, 11, 15-27.*
Tanji et al. "Therapeutic use of phage cocktail for controlling *Escherichia coli* O157:H7 in gastrointestinal tract of mice". Journal of Bioscience and Bioengineering. 2005, vol. 100, No. 3, pp. 280-287.*
International Search Report and Written Opinion for International Application No. PCT/GB2013/051163, dated Aug. 6, 2013, 8 pages.
Abedon, S. T. et a., "Bacteriophage plaques: theory and analysis," Methods Mol. Biol., 501:161-174 (2009).
Bielke, L. et al., "*Salmonella* host range of bacteriophages that infect multiple genera," Poult. Sci., 86(12):2536-2540 (2007).
Gill, J. J. et al., "Phage choice, isolation, and preparation for phage therapy," Curr. Pharm. Biotech., 11(1):2-14 (2010).
Goodridge, L. D. et al., "Desiging phage therapeutics," Curr. Pharm. Biotechnol., 11(1):15-27 (2010).
Guidolin, A. et al., "Bacteriophage CP-T1 of Vibrio cholerae. Identification of the cell surface receptor," Eur. J. Biochem., 153(1):89-94 (1985).
Harper, D. R. et al., "Phage therapy: delivering on the promise," Therapeutic Delivery, 2(7):935-947 (2011).
Hausler, T., "Viruses vs. Superbugs: A solution of the Antibiotics Crisis?", MacMillan Science e-book, pp. 1-309 (2006).
Huff, W. E. et al., "Alternatives to antibiotics: utilization of bacteriophage to treat colibacillosis and prevent foodborne pathogens," Poult Sci., 84(4):655-659 (2005).
Jamalludeen, N. et al., "Evaluation of bacteriophages for prevention and treatment of diarrhea due to experimental enterotoxigenic *Escherichia coli* O149 infection of pigs," Vet Microbiol., 136(1-2):135-141 (2009).
Pirsi, A., "Phage therapy—advantages over antibiotics?" The Lancet, 356(9239):1418 (2000).
Roy, B. et al., "Biological inactivation of adhering listeria monocytogenes by listeriaphages and a quaternary ammonium compound," Appl, Environ. Microbiol., 59(9):2914-2917 (1993).

(Continued)

*Primary Examiner* — Vera Afremova

(74) *Attorney, Agent, or Firm* — Mintz, Levin, Cohn, Ferris, Glovsky and Popeo, P.C.

(57) ABSTRACT

The present invention provides methods of designing panels of bacteriophages as therapeutic compositions against bacterial infections. The present invention also provides panels of bacteriophages for use in the prevention or treatment of bacterial infections.

6 Claims, 15 Drawing Sheets

(56) References Cited

OTHER PUBLICATIONS

Wright, A. et al., "A controlled clinical trial of a therapeutic bacteriophage preparation in chronic otitis due to antibiotic-resistant Pseudomonas aeruginosa; a preliminary report of efficacy," Clinical Otolarynaology, 34(4):349-357 (2009).
Tanji, Y. et al., "Toward rational control of *Escherichia coli* O157:H7 by a phage cocktail," Appl. Microbiol. Biotechnol., 64:270-274 (2004).

* cited by examiner

FIGURE 1

Table 1

| Phage | Bacterial host | Stock titre (pfu/ml) | Plaque formation on PAK | Sensitivity test / Good plating efficiency based on plaque assay results? PAK | Platereader assay (MOI 0.1 in PAK) |
|---|---|---|---|---|---|
| BCP1 | BC12 | 4.3E+10 | S | Yes | |
| BCP2 | BC254 | 1.0E+08 | I | No | |
| BCP3 | BC15 | 6.0E+09 | R | No | |
| BCP4 | BC207 | 5.0E+09 | I | Yes | |
| BCP6 | BC15 | 4.5E+10 | S | No | |
| BCP12 | BC3 | 3.7E+10 | S | Yes | |
| BCP14 | BC207 | 6.0E+09 | S | Yes | |
| BCP21L | BC178 | 1.6E+10 | S | No | |
| BCP29 | BC14 | 1.4E+10 | S | Moderate | |
| BCP33 | BC230 | 6.2E+10 | I | No | |
| BCP37 | BC193 | 3.5E+08 | S/I | No | |
| BCP62 | BC191 | 2.8E+08 | R | No | |
| BCP69 | BC254 | 1.9E+10 | I | No | |
| BCP154 | BC725 | 1.1E+10 | S | No | |

FIGURE 3

Table 3

| Phage | MOI | OD600 over 24 h and endpoint OD600 | | | Mean OD600 |
|---|---|---|---|---|---|
| no phage | - | 2.09 | 2.12 | 2.19 | 2.13 |
| BCP1 BCP37 | 0.1 | 1.04 | 1.10 | 1.05 | 1.06 |
| BCP12 BCP37 | 0.1 | 1.11 | 1.18 | 1.28 | 1.19 |
| BCP1 BCP12 BCP37 | 0.1 | 0.95 | 0.94 | 0.95 | 0.95 |
| BCP12 BCP14 BCP37 | 0.1 | 1.39 | 1.57 | 1.38 | 1.45 |

FIGURE 6

| Phage | Growth strain | MOI | OD600 over 24 h |
|---|---|---|---|
| BCP12_PAK<br>BCP37_BC00193<br>BCP6_BC00015 | | 1 | |
| BCP12_PAK<br>BCP37_BC00193<br>BCP21L_BC00178 | | 1 | |
| BCP12_PAK<br>BCP37_BC00193<br>BCP26_BC00010 | | 1 | |
| BCP12_PAK<br>BCP37_BC00193<br>BCP28_BC00014 | | 1 | |
| BCP12_PAK<br>BCP37_BC00193<br>BCP45_BC00237 | | 1 | |

Table 6

Numbers show mean whole body fluorescence counts for each group

Luminescence in infected mice from 6 to 24 hours.

Bacteriophage counts in the mouse lung (bacteriophage treated sample only).

THERAPEUTIC BACTERIOPHAGE COMPOSITIONS

This patent application claims priority to GB 1207910.9 filed on 4 May 2012, and to GB 1218083.2 filed on 9 Oct. 2012, which are hereby incorporated by reference in their entirety.

FIELD OF THE INVENTION

The present invention relates to methods for preparing panels of bacteriophages (whether as a premixed cocktail or for mixing prior to use).

BACKGROUND TO THE INVENTION

Antibiotic resistance is now seen as one of the major challenges facing modern medicine. Given the shortage of novel antibiotics, a number of alternative approaches are being investigated, including the use of bacteriophages as therapeutic agents (Harper, Anderson & Enright, Therapeutic Delivery (2011), 2, 935-947; Hausler T, Viruses vs. Superbugs: A Solution to the Antibiotics Crisis? (2006) MacMillan, New York.

Bacteriophages (often known simply as "phages") are viruses that grow within bacteria. The name translates as "eaters of bacteria" and reflects the fact that as they grow most bacteriophages kill the bacterial host as the next generation of bacteriophages is released. Early work with bacteriophages was hindered by many factors, one of which was the widespread belief that there was only one type of bacteriophage, a non-specific virus that killed all bacteria. In contrast, it is now understood that the host range of bacteriophages (the spectrum of bacteria they are capable of infecting) is often very specific. This specificity, however, has the disadvantage that it is difficult to achieve breadth of adequate bacteriophage efficacy across bacterial target species/strains. There is therefore a need in the art for methods of identifying improved combinations of bacteriophages having effective targeting capability in relation to bacterial species/strains—see, for example, Pirsi, The Lancet (2000) 355, 1418. For these reasons, examples of phage compositions demonstrating sound clinical efficacy are very limited. By way of example, reference is made to Applicant's successful clinical trials (veterinary and human) conducted with a panel of bacteriophages that target *Pseudomonas aeruginosa*—see Wright et al, Clinical Otolaryngology (2009) 34, 349-357. There is therefore a need in the art to develop further panels of bacteriophages that have optimal clinical applicability.

In particular, there is a need in the art to design panels of two or more bacteriophages that target the same bacterial host species/strain, wherein said panel of bacteriophage provide adequate efficacy against a bacterial target species/strain when compared to the individual efficacy of said bacteriophage against said bacterial target species/strain. In this regard, it is necessary that the bacteriophage members of the panel work well together in a combination (e.g. the panel demonstrates equivalent or improved efficacy vis-à-vis the individual members thereof).

The present invention addresses one or more of the above problems.

SUMMARY OF THE INVENTION

The present invention solves the above described problems by providing methods for designing panels of bacteriophages, as specified in the claims. The present invention also provides panels of bacteriophages and uses thereof, as specified in the claims.

In one aspect, the present invention provides a method for designing an optimal therapeutic panel of bacteriophages (comprising two or more bacteriophages). Said method includes assaying the activity of individual bacteriophages in liquid cultures of a target bacterial species/strain to determine the kinetics of bacterial growth, together with the development and specificity of resistance developed by the bacterial target in said culture. The method further includes determining the efficacy of bacteriophage panels in said culture, and thus identifying an advantageous bacteriophage panel for use against the target bacterial species/strain.

BRIEF DESCRIPTION OF THE DRAWINGS

FIG. 1 is a table showing the results of screening individual bacteriophages by plaque assay and in liquid culture. MOI= multiplicity of infection (ratio of infecting bacteriophage to bacterial host cells).

FIG. 3 is a table showing results that clarify the antagonistic effects of bacteriophage BCP14 to bacteriophage BCP37 in reducing the development of bacterial resistance.

FIG. 6 is a table showing data evaluating all candidate bacteriophages in mixtures with BCP12 and BCP37.

DETAILED DESCRIPTION

Figure 2:
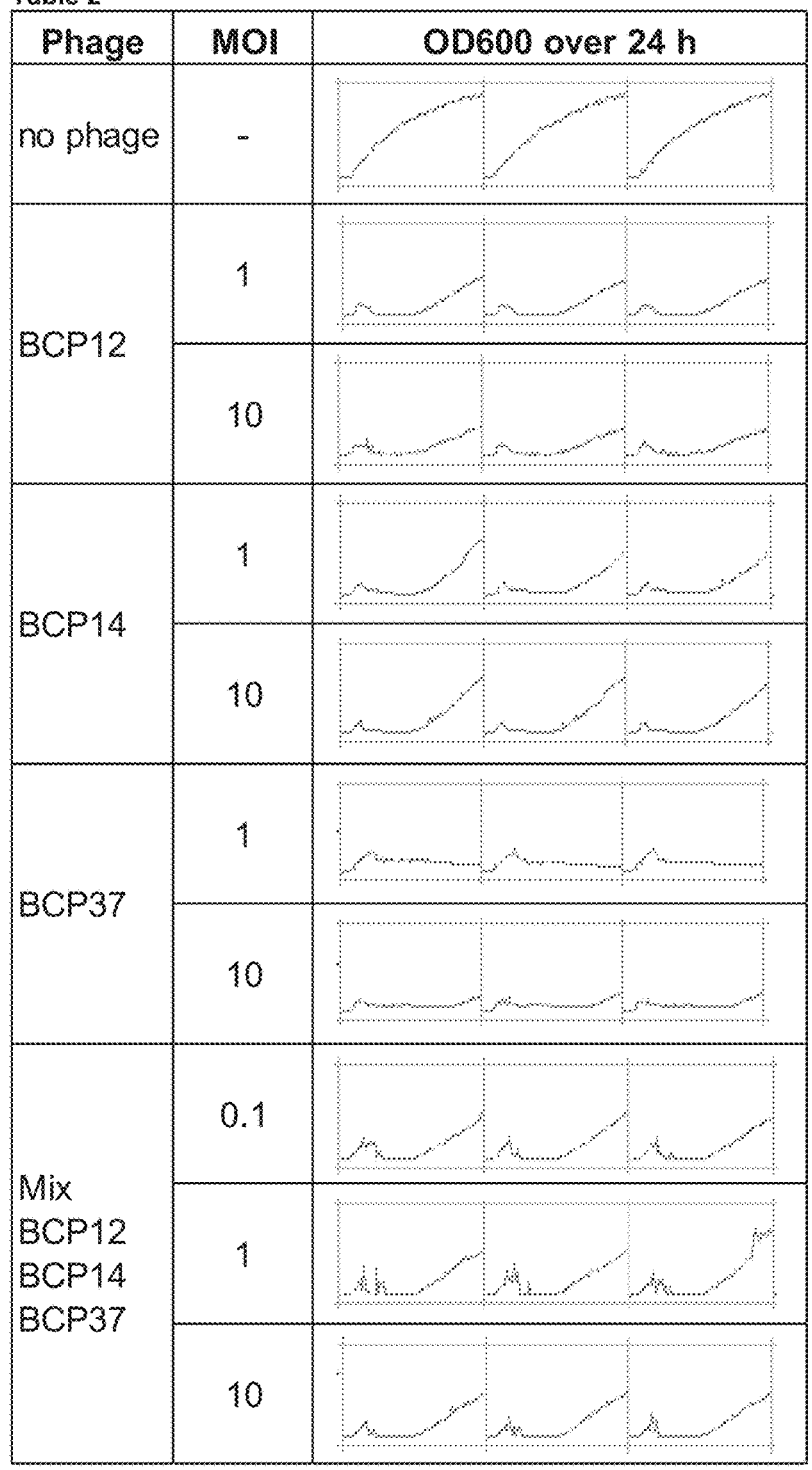
FIG. 2 is a table showing results from re-testing of bacteriophages BCP12, BCP14 and BCP37 individually at higher MOI and as a mixture.

Bacteriophages that infect the same bacterial species/strain may employ similar mechanisms of infection, meaning that resistance of the bacterial species/strain to one bacteriophage confers cross-resistance to other bacteriophages—see Gill & Hyman, Curr. Pharm. Biotech. (2010) 11, 2-14; and Guidolin & Manning, Eur. J. Biochem (1985)

153, 89-94. Clearly this is undesirable. Additionally, the present inventors have unexpectedly identified that bacteriophages can be antagonistic towards one another when targeting a given bacterial species/strain, thereby limiting the effect of co-infecting bacteriophages.

In one aspect, the present invention therefore provides a method for designing a panel of bacteriophages (comprising two or more bacteriophages), which minimises target bacterial species/strain resistance to each of said individual bacteriophages (i.e. cross-resistance) in the panel, and/or antagonism between said bacteriophages when targeting the bacterial species/strain. Said method employs a process of measuring bacterial target growth characteristics and/or bacteriophage growth characteristics when present in liquid cultures of their host (target) bacteria, following by selection of a therapeutic panel of bacteriophages.

Individual lytic bacteriophages may be tested in plaque assay and/or in liquid (broth) culture with their bacterial host—both tests are preferably employed (e.g. one test may be performed sequentially or prior to the next, or both may be performed substantially simultaneously). Those that show efficient killing of the bacterial host in these two systems are not necessarily identical. By way of example, plaque assay is a complex dynamic process (Abedon & Yin, Methods Mol. Biol. (2009) 501, 161-174), whereas broth culture provides a less structured environment in which to monitor lysis (killing) of the bacterial host.

Bacterial numbers in such liquid cultures may be monitored directly by viable count of an aliquot of the culture medium. Alternatively, bacterial numbers may be measured by assaying the optical density of the culture. By way of example, plate reader systems allow such cultures to be monitored directly in high throughput systems, typically with optical density measured at 600 nm.

In liquid cultures not treated with bacteriophage, bacterial numbers increase over several hours, eventually slowing as nutrients are exhausted and bacterial numbers reach a maximum level. When treated with bacteriophage, bacterial numbers typically increase for a short time then decline rapidly. However, when treated with a single (e.g. a first) bacteriophage (or a mixture of bacteriophages where cross-resistance occurs) after several hours resistant bacteria start to appear and bacterial numbers again increase.

By sampling these resistant bacteria and assaying the effect of different bacteriophages (e.g. second and/or third bacteriophages, etc.) on them, bacteriophages (e.g. second and/or third different bacteriophages, etc.) are identified where bacterial resistance to one phage (e.g. the first phage) does not confer resistance to others phages (e.g. second and/or third different bacteriophages, etc.)—referred to herein as a lack of cross-resistance to phage. The selection and use of bacteriophage panels comprising bacteriophages that demonstrate a lack of cross-resistance to a target bacterial species/strain is highly desirable in bacteriophage panels designed for use as an anti-microbial therapeutic.

Once a panel of bacteriophages (having desired characteristics as hereinbefore identified), the panel may then be tested in liquid culture. Surprisingly, some mixtures of individual bacteriophages do not necessarily produce additive effects. In particular, antagonism occurs where the effects of combined phages are less effective at reducing bacterial numbers than are achieved with the corresponding individual bacteriophages in isolation. Monitoring the efficacy of such mixtures in reducing bacterial numbers in liquid culture provides a means of identifying such antagonistic combinations, which are considered non-optimal for further development as candidate therapeutics.

Methods for determining growth of bacteria (such as a target bacterial species or strain) are known in the art. By way of example, growth can be determined of a target bacterial species or strain growing in a culture, such as a liquid culture. In this regard, as the bacteria multiply and increase in number, the optical density of the liquid culture increases (due to the presence of an increasing number of bacterial cells). Thus, an increase in optical density indicates bacterial growth. Optical density may be measured at 600 nm ($OD_{600}$). For example, optical density at 600 nm can be determined within the wells of a multi-well plate (e.g. a 96-well plate) using an automated plate reader (for example a BMG Labtech FLUOstar Omega plate reader).

Growth of a target bacterial species or strain can be determined and/or monitored over a defined time period (for example, at least 2, 4, 8, 12, 16, 20, 24, 36 or 48 hours).

In some embodiments, a time period may be defined as starting from the addition of one or more different bacteriophages to a target bacterial species or strain. Alternatively, a time period may be defined as starting at a predetermined point after the addition of one or more different bacteriophages to a target bacterial species or strain (for example, starting at least 0.25, 0.5, 1, 1.5, 2, 3, 4, 6, 8, 10 or 12 hours after).

Methods of determining if a bacteriophage or combination of bacteriophages retards growth (i.e. effects growth retardation) of a given population of bacteria (for example, a target bacterial species or strain, as specified in the claims; or a resistant culture, as specified in the claims) are known in the art.

As a bacteriophage (or combination of bacteriophages) multiplies in host bacteria, bacterial lysis occurs, killing bacteria and leading to a decrease in bacterial growth. A decrease in bacterial growth can include a decrease in the rate of growth (e.g. the rate at which the bacterial cell number increases), a cessation of growth (such that the bacterial cell number remains constant), or a decrease in the total bacterial cell number.

In one embodiment, growth retardation (i.e. when a bacteriophage or combination of bacteriophages retards growth) means that bacterial growth in the presence of a given bacteriophage or combination of bacteriophages is decreased as compared to bacterial growth of an equivalent population of bacteria (under the same or equivalent conditions) in the absence of said bacteriophage or combination of bacteriophages.

Methods for determining bacterial growth are known in the art, as described above. Thus, methods used to determine bacterial growth (e.g. through measurement of bacterial numbers) may also be used to determine growth retardation. Thus, by way of example, growth retardation may be determined at a specified time point or over a specified period of time following addition of a bacteriophage or combination of bacteriophages to a bacterial population (for example, at least 2, 4, 8, 12, 16, 20, 24, 36 or 48 hours). By way of example, the specified period of time may embrace the logarithmic phase of bacterial growth.

In one embodiment, wherein the invention provides a method of designing a panel of bacteriophages as a therapeutic composition against a bacterial infection, as specified in any of claims 1-4, if a combination of bacteriophages retards growth of the target bacterial species or strain at least equal to the greatest growth retardation achieved independently by any one of said two or more different bacteriophages, the combination is accepted as a panel of bacteriophages, and the bacteriophages which make up said combination are deemed to lack antagonism.

Methods for determining the development of bacterial resistance against a bacteriophage or combination of bacteriophages are known in the art. By way of example, the development of bacterial resistance may be determined by monitoring bacterial growth in the presence of a bacteriophage or combination of bacteriophages. Bacterial growth may be monitored as described above. Thus, in the absence of bacterial resistance against the bacteriophage or combination of bacteriophages, growth retardation (as described above) may be observed. As bacterial resistance develops, the effects of growth retardation are overcome and bacterial growth increases. The development of bacterial resistance may be determined by monitoring bacterial growth for a specified period of time, as described above (for example, at least 2, 4, 8, 12, 16, 20, 24, 36 or 48 hours).

Determining the development of bacterial resistance can also allow the identification of combinations of bacteriophages wherein bacterial resistance to one bacteriophage does not confer resistance to another bacteriophage in the combination (referred to as a lack of cross-resistance, as described above).

Thus, in one embodiment, wherein the invention provides a method of designing a panel of bacteriophages as a therapeutic composition against a bacterial infection if said second bacteriophage retards growth of the first resistant bacterial culture, the target bacterial species or strain is deemed to lack cross-resistance to the combination of said first and second bacteriophages.

In another embodiment, wherein the invention provides a method of designing a panel of bacteriophages as a therapeutic composition against a bacterial infection if said third bacteriophage retards growth of the second resistant bacterial culture, the target bacterial species or strain is deemed to lack cross-resistance to the combination of at least said second and third bacteriophages; preferably, the target bacterial species or strain is deemed to lack cross-resistance to the combination of said first, second and third bacteriophages.

EXAMPLES

A mixture for in vivo use was developed against the PAK strain of *Pseudomonas aeruginosa*. The stages of this development exemplify the stages of the invention.

Initial Screening:

The *Pseudomonas aeruginosa* strain PAK is used in studies of mouse lung infection, using an inserted luminescent reporter gene to identify non-invasively the sites and levels of infection.

To identify bacteriophages for a therapeutic bacteriophage mix for use against the PAK strain, bacteriophages grown on permissive host strains were then tested against the PAK strain by spot testing on bacterial lawns, enumerative plaque assay and broth culture using a plate reader assay system. The plate reader monitors intensively the optical density of a broth culture containing bacteriophages with a suitable host in a multi-well plate format. This latter method allows detailed kinetics of the infection process to be evaluated.

Screening of individual bacteriophages by plaque assay and in liquid culture produced the results shown in FIG. 1 (Table 1). [MOI=multiplicity of infection (ratio of infecting bacteriophage to bacterial host cells)].

The marked discrepancy between the poor plaque formation by bacteriophage BCP37 and its efficacy in liquid culture are to be noted.

Based on the data shown in FIG. 1 (Table 1), bacteriophages BCP1, BCP12, BCP14 and BCP37 were selected for further investigation.

Bacteriophage Propagation and Purification:

Candidate bacteriophages were propagated in liquid (broth) culture and lysates prepared from these for further work. Clarified lysates were purified by centrifugation through a sucrose cushion (27 ml of each lysate is carefully over-layered onto 5 ml of a sterile 10% w/v sucrose 'cushion', in 36 ml polypropylene tubes prior to centrifugation. The sucrose 'cushion' helps to remove endotoxins, while allowing the virus particles to pellet at the bottom of the tube. Bacteriophage pellets were resuspended in phosphate-buffered saline (PBS) and passed through a 0.2 μM syringe filter to ensure sterility.

Initial Testing of Bacteriophage Mixtures:

The individual bacteriophages BCP12, BCP14 and BCP37 were then retested both individually at higher MOI and as a mixture, with results shown in FIG. 2 (Table 2).

The results of this testing were surprising. As can be seen from the data shown in FIG. 2 (Table 2), bacteriophage BCP37 produced effective reduction of bacterial host numbers with very limited development of resistance. Bacteriophages BCP12 and BCP14 permitted more development of resistance. However, when a mixture of all three bacteriophages were used, while bacterial numbers were controlled initially, the development of resistant forms was clearly more rapid than with BCP37 alone, indicating antagonistic effects in the mixed bacteriophage infection that permit enhanced bacterial escape.

Further testing clarified that bacteriophage BCP14 appeared to be specifically antagonistic to the effects of bacteriophage BCP37 in reducing the development of bacterial resistance; data are shown in FIG. 3 (Table 3).

The final optical density value (OD600) given in FIG. 3 (Table 3) reflects the development of bacterial resistance after 24 hours. With mixtures of BCP 37 with BCP1 or BCP12, this was greatly reduced compared to untreated controls. This reduced still further when a mixture of all three bacteriophages (BCP1, BCP12, BCP37) is used. However, when bacteriophage BCP14 is used instead of BCP1, the final OD600 (and thus bacterial number) is markedly higher, illustrating the antagonistic effect.

Figure 4:
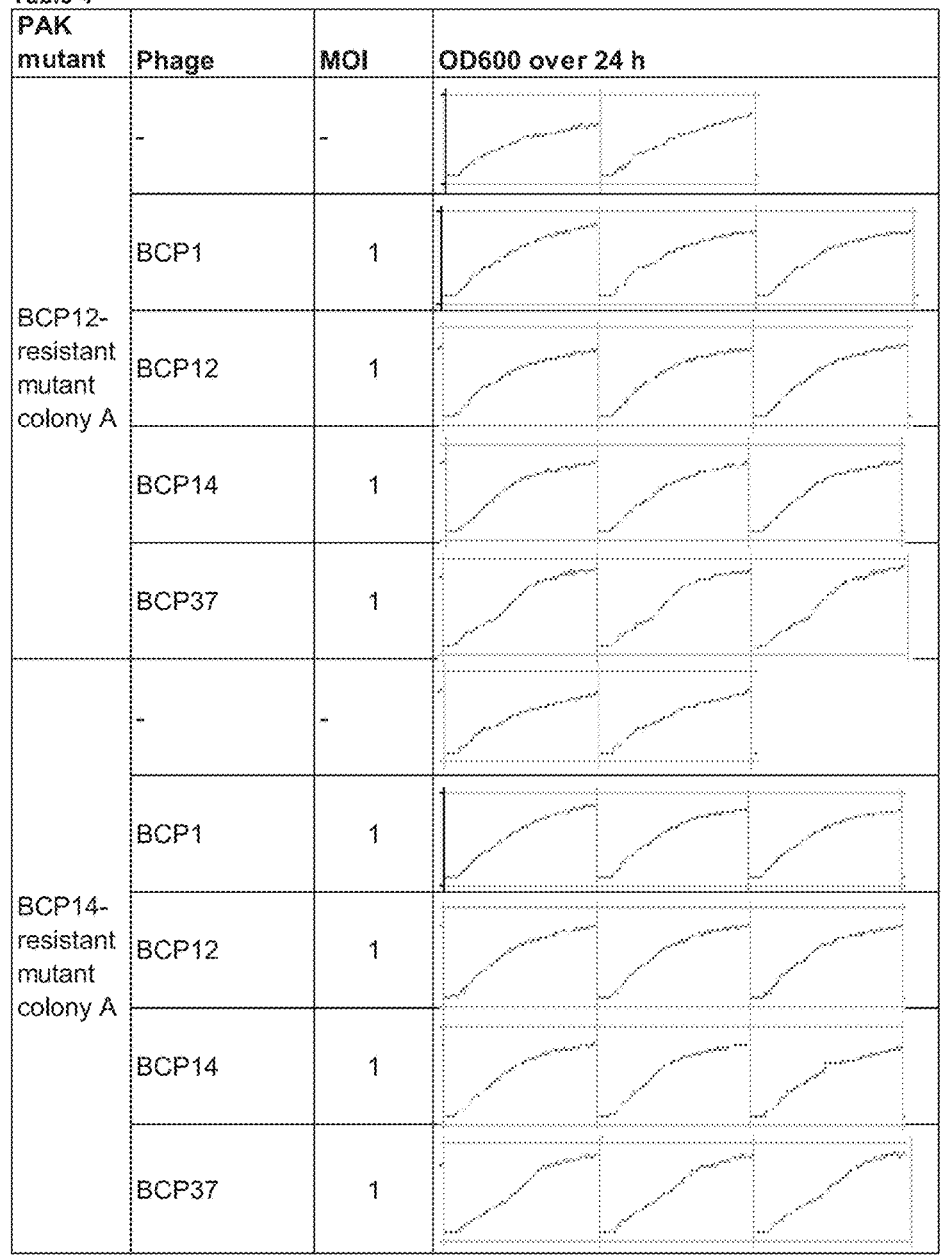
FIG. 4 is a table showing results from resistant escape mutants from each assay treated with the other candidate bacteriophages.
Figure 4:
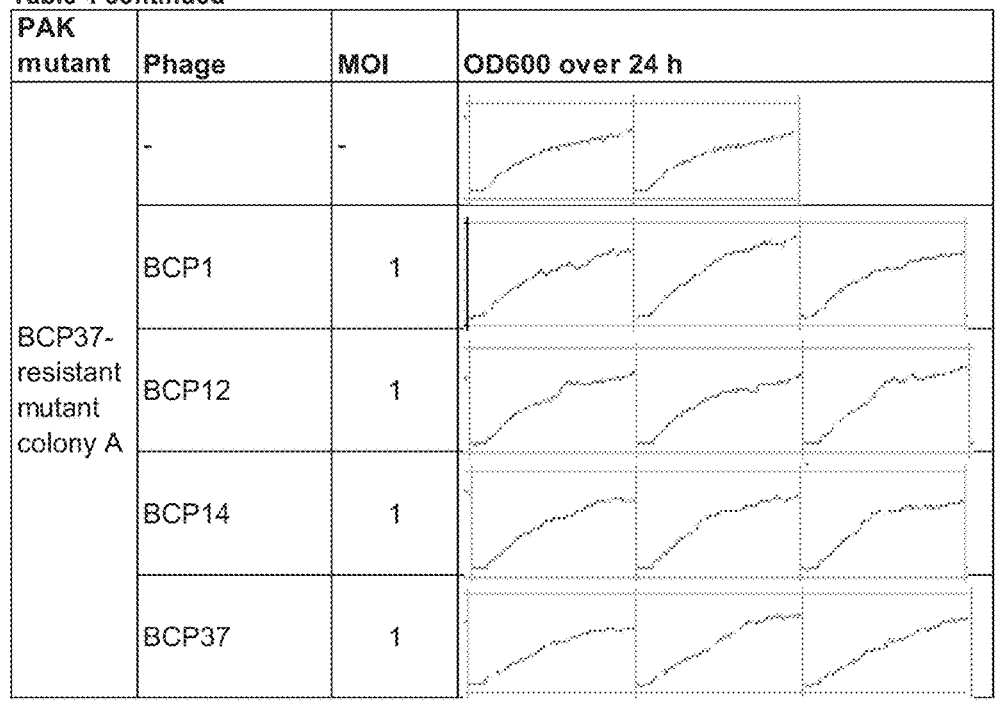

Identification of Cross-Resistance:

Host bacteria that had developed resistance to the bacteriophage that they were treated with showed marked growth by 24 hours after infection. In order to determine whether the observed effects with initial bacteriophage mixtures were due to cross-resistance, resistant ("escape") mutants from each assay were harvested and were treated with the other candidate bacteriophages. This showed that resistant forms to each of the four bacteriophages were also resistant to all of the others; data are shown in FIG. 4 (Table 4).

Thus, all four bacteriophages (BCP1, BCP12, BCP14, BCP37) fall into the same complementation group and allow the generation of common cross-resistant forms of the host bacteria. It was thus desirable to identify at least one bacteriophage which did not permit the development of such cross-resistance.

Figure 5:
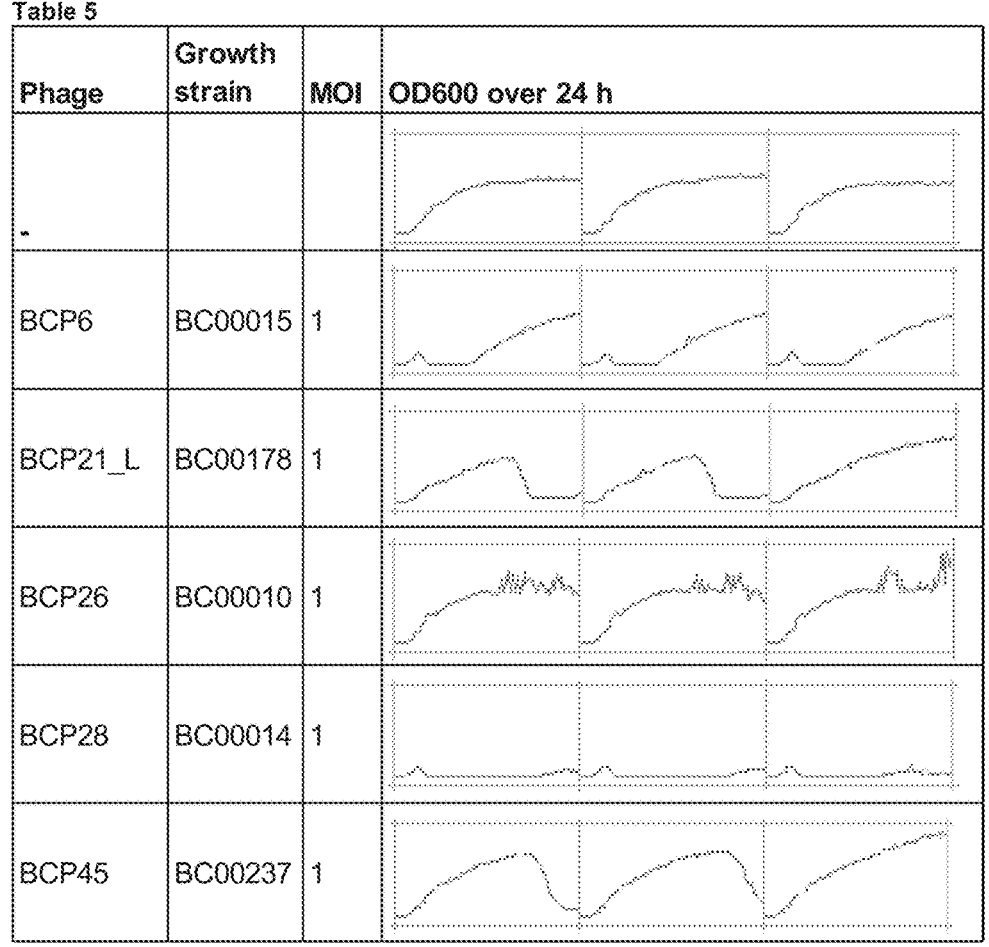
FIG. 5 is a table showing activity data of bacteriophages BCP6, BCP21L, BCP26, BCP28 and BCP45 against BCP37-resistant PAK in liquid culture.

Evaluation of Additional Bacteriophages:

Since PAK mutants that developed resistance to individual candidate bacteriophages showed cross-resistance to other bacteriophages in the test group, additional bacteriophages were screened to identify candidates from existing stocks that would not be compromised by the same resistance mechanism. Sensitivity testing identified bacteriophages BCP6, BCP21L, BCP26, BCP28 and BCP45 as showing activity against both BCP12-resistant and BCP37-resistant PAK mutants. The activity of these bacteriophages against PAK in liquid culture was evaluated; data are shown in FIG. 5 (Table 5).

These results indicated that BCP28 was the most promising candidate, showing similar effects to BCP37 with minimal development of resistance.

All candidate bacteriophages were then evaluated in mixtures with BCP12 and BCP37, data are shown in FIG. 6 (Table 6).

Despite the limited effects of BCP6, BCP21L, BCP26 and BCP45 in individual assays they were relatively effective in the mixtures. BCP6 and BCP 28 showed the most limited development of resistance.

Given its apparent superiority in individual culture, BCP28 was selected for the candidate therapeutic mixture, to be combined with BCP12 and BCP37. This mixture (the three-phage mixture) thus has three bacteriophages from two complementation groups.

Figure 7:
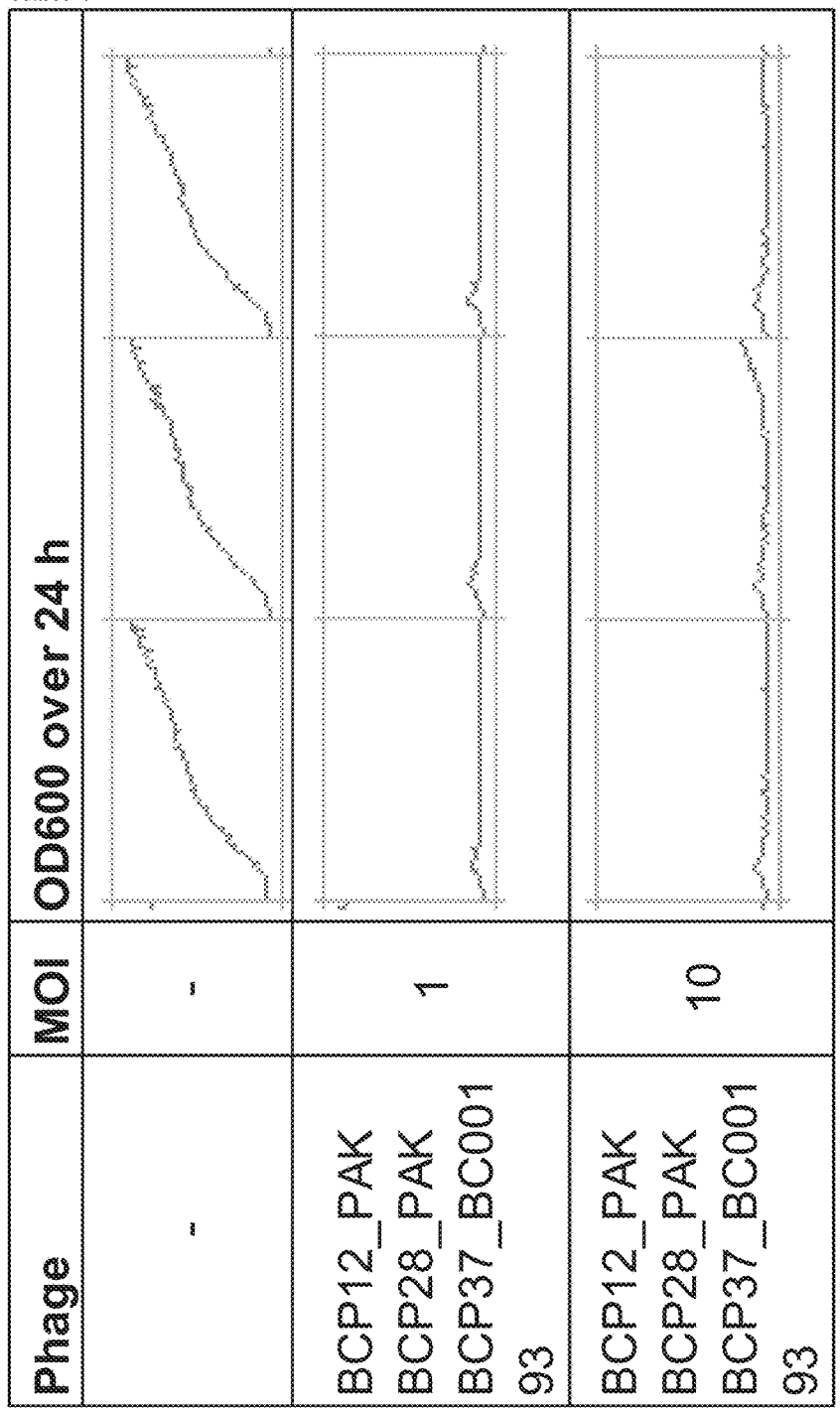
FIG. 7 is a table showing the final evaluation of a candidate mixture of three bacteriophages producing rapid and effective killing of the bacterial target and markedly limited the development of bacterial resistance.
Figure 8:
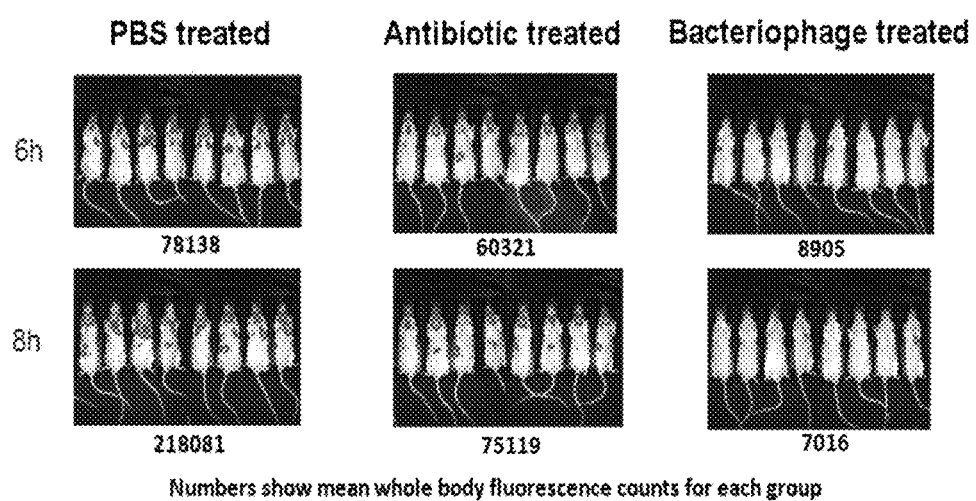
FIG. 8 shows fluorescence imaging of control (PBS), antibiotic and bacteriophage treated mice at 6 hour and 8 hour time points. The antibiotic used was ciprofloxacin and the numbers below each picture show mean whole body fluorescence counts for each group.
Figure 9:
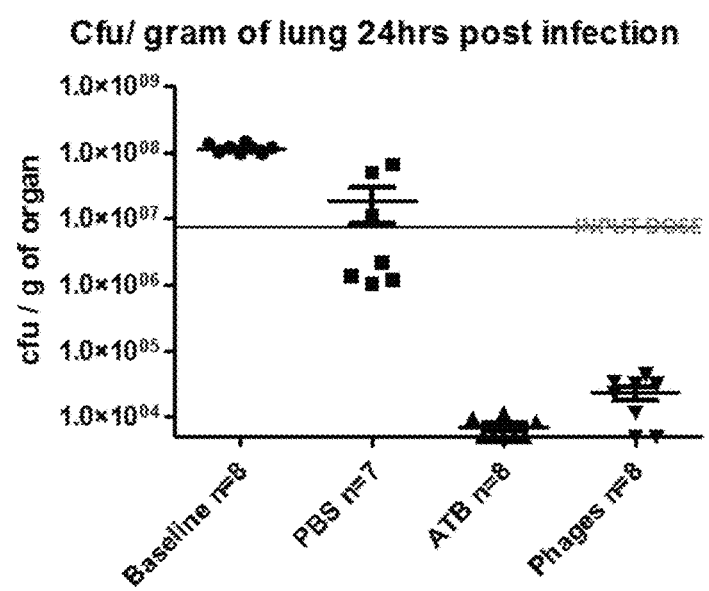
FIG. 9 shows a graph of the enumeration of bacteria in the lung 24 hours post infection in control (PBS), antibiotic, and bacteriophage treated mice. ATB=ciprofloxacin.
Figure 10:
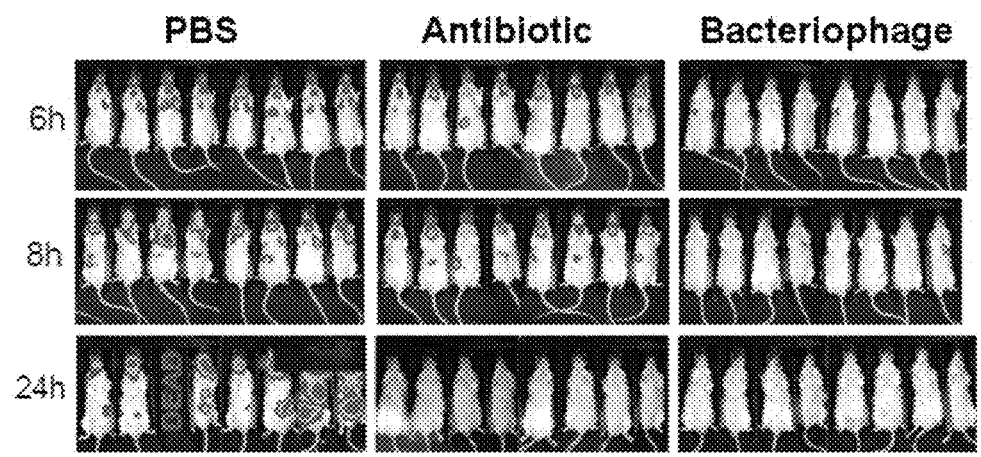
FIG. 10 shows fluorescence imaging of control (PBS), antibiotic and bacteriophage treated mice at 6 hour, 8 hour, and 24 hour time points. The antibiotic used was ciprofloxacin.
Figure 11:
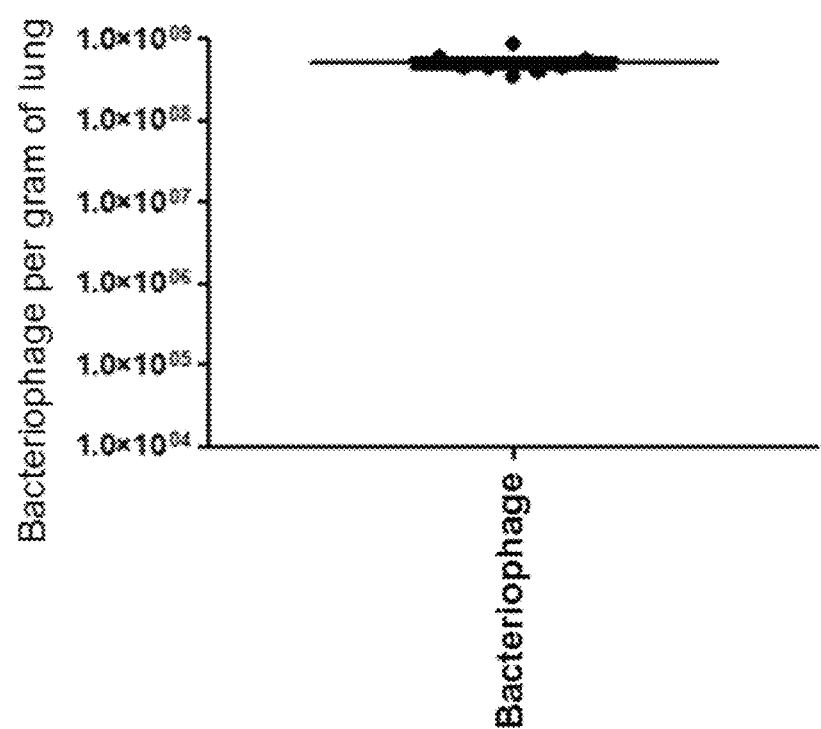
FIG. 11 shows a graph of the enumeration of bacteriophages in the lung of bacteriophage treated mice.
Figure 12A:
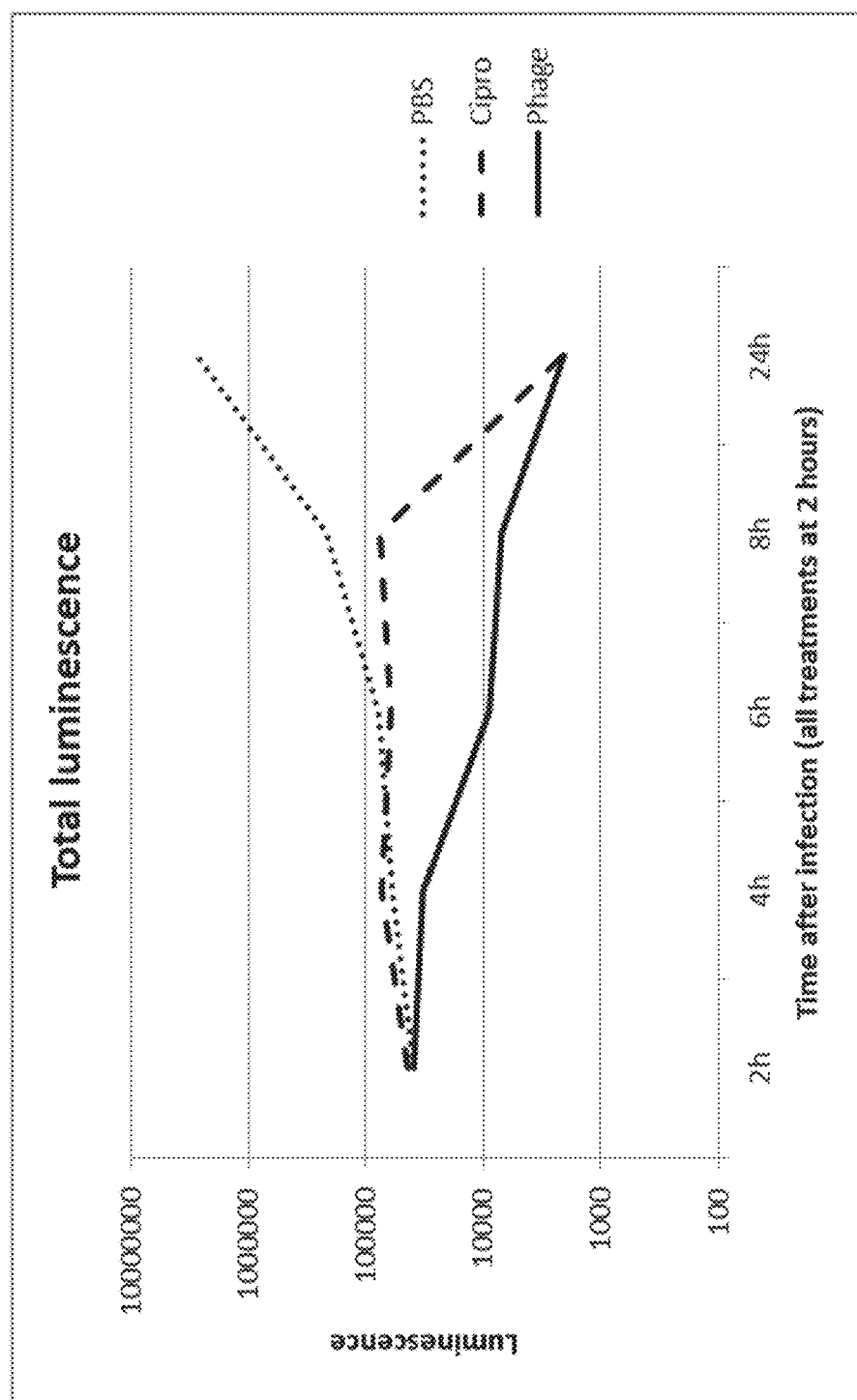
FIG. 12 presents graphs showing: 12*a* total, 12*b* oronasal, and 12*c* lung luminescence (respectively) of infected mice as a function of time after infection. Each graph presents data for mice administered with a control (PBS), ciprofloxacin, and bacteriophages, respectively.
Figure 12B:
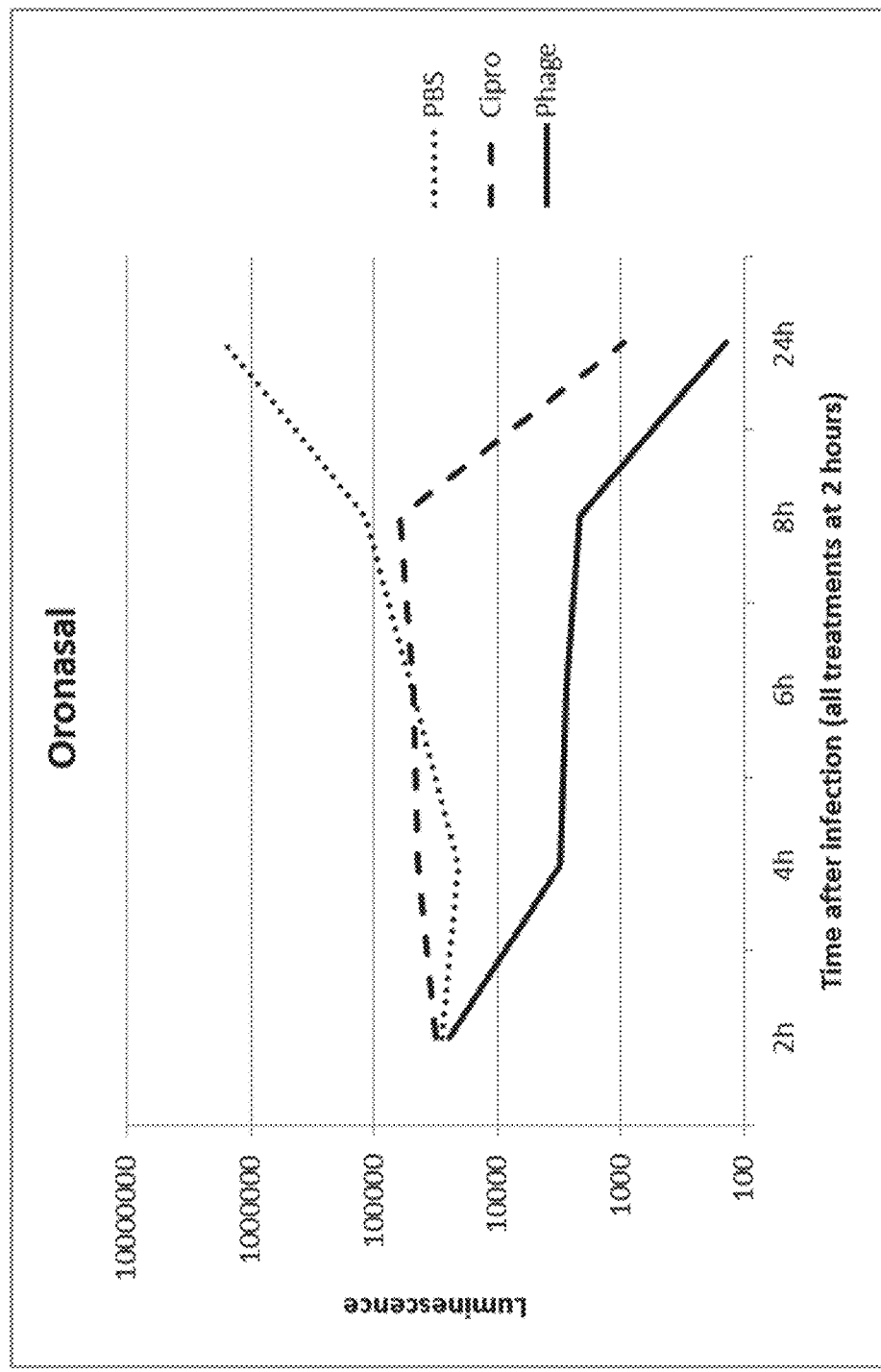
Figure 12C:
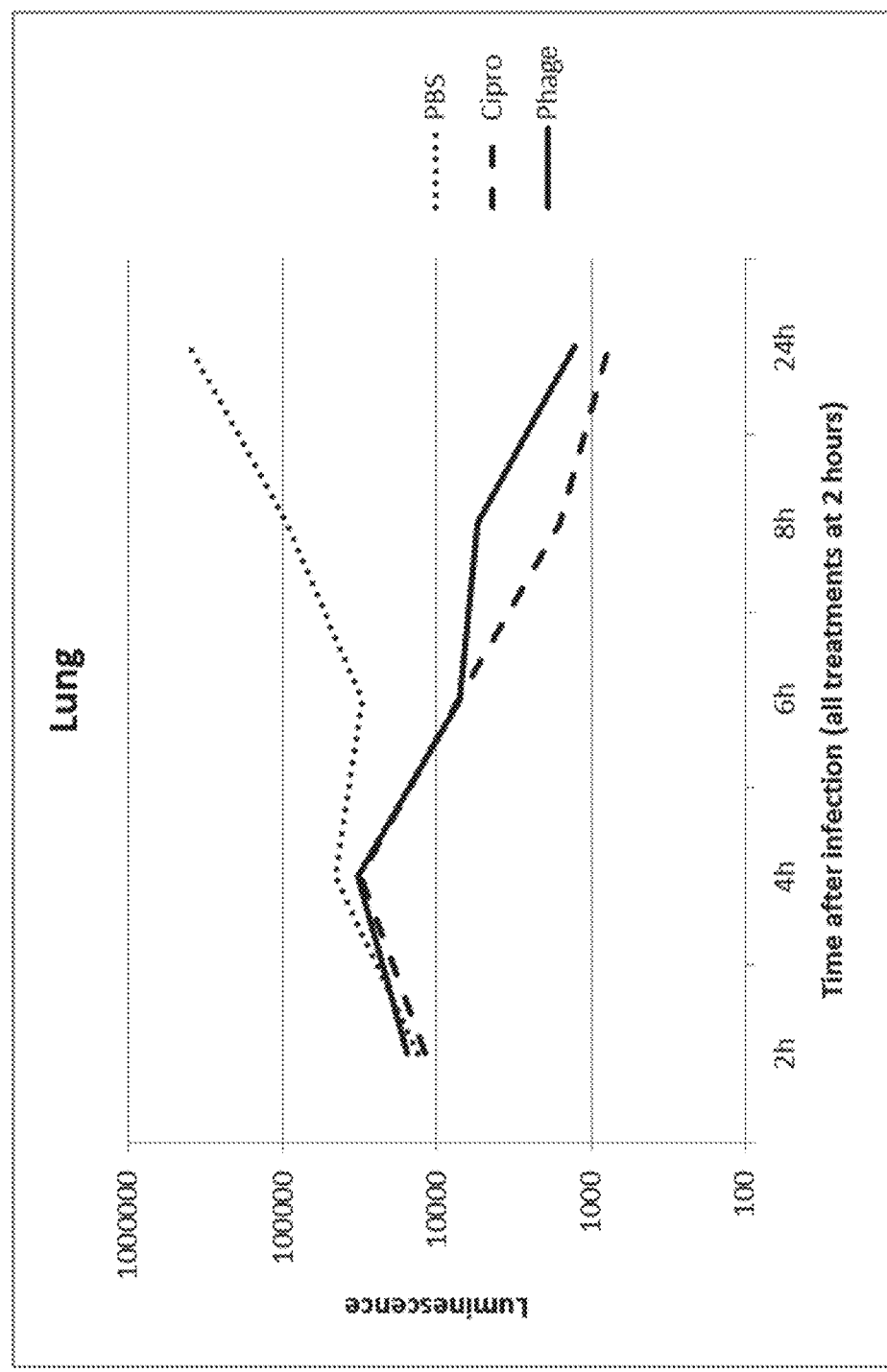

Final Evaluation of the Candidate Therapeutic Mixture In Vitro:

Data from the final evaluation are shown in FIG. 7 (Table 7).

Thus, a candidate mixture of three bacteriophages was identified which "flatlined" the growth of the host bacteria, producing rapid and effective killing of the bacterial target and markedly limited the development of bacterial resistance.

In Vivo Evaluation of the Three-Phage Mix:

The three bacteriophages were purified as noted above and combined for use in an in vivo study where infection was established using a luminescent strain of PAK (PAK-lumi).

Lytic bacteriophages with efficacy against *P. aeruginosa* PAK strain were assayed in liquid cultures of host bacteria, addressing both cross-resistance and apparent antagonism between specific bacteriophages in the development of an optimised therapeutic mixture. Three selected bacteriophages were mixed and used in an in vivo study where infection was established using a luminescent strain of PAK (PAK-lumi).

Four groups of eight BALB/C mice were infected intranasally with PAK-lumi and treated as follows:

All 32 mice were infected intranasally with $9 \times 10^6$ CFU in 25 µl of PAK Lumi in PBS Group 1 (n=8): Imaged and euthanized at t=2 hrs post infection Group 2 (n=8): Imaged and treated with PBS at t=2 hrs post infection Group 3 (n=8): Imaged and treated with 200 mg/kg of ciprofloxacin 2 hrs post infection in subcutaneous injection, imaged at 2, 4, 6, 8 and 24 hrs post infection and euthanized at 24 hrs post infection (this is an extremely high dose)

Group 4 (n=8): Imaged and treated intranasally with 30 µl of the three-phage mix, at 2 hrs post infection, imaged at 6 and 8 hours post infection and euthanized at 24 hrs post infection. Mice were observed for clinical signs and infection luminescence—measured using an IVIS in vivo imaging system. At 24 h animals were euthanized and lung homogenate CFU/PFU determined.

Efficacy of the three-phage mix in vivo was demonstrated by both fluorescence imaging and by enumeration of bacteria in the lung (Antibiotic=ATB=Ciprofloxacin as stated) [FIGS. 8-12].

The efficacy of the three-phage mix derived using the method as presented was confirmed in vivo.

The bacteriophage mix showed potent activity and no resistance in vitro at 24 hours. in vivo, bacteriophage-treated mice showed a marked decrease in luminescence after 6 h with greater reduction overall compared with the ciprofloxacin group. This was particularly notable in the nasopharyngeal area, although reductions were also seen in luminescence with the abdominal area. Luminescence in the lungs was broadly comparable, but was markedly reduced with both ciprofloxacin and the bacteriophage mixture. By 24 h all phage and antibiotic treated mice survived with ~3 log. reduction in lung CFU observed for both groups.

In conclusion:

The three-phage mix is highly effective in vitro.

It is also able to rapidly control bacteria in the oropharynx and lungs of mice infected by the PAK strain of *P. aeruginosa* in an acute phase model.

Its efficacy is equivalent or superior to a high dose of an antibiotic proven to be active against the infecting organism.

Its action appears to be faster than the antibiotic, and the dissemination of the infection is reduced.

Moving on from this acute model, both laboratory biofilm studies and clinical trial data from the chronically infected ear suggests that a heavily colonised, biofilm-rich environment can provide the optimal conditions for bacteriophage therapy.

The cystic fibrosis lung may provide such an environment.

The invention claimed is:

1. A method of designing a panel of bacteriophages as a therapeutic composition for treating a bacterial infection, the method comprising:
   (a) providing at least three different bacteriophages, wherein each of said different bacteriophages retards growth of a target bacterial strain;
   (b) combining said at least three different bacteriophages to provide a first bacteriophage panel; and
   (c) determining growth of the target bacterial strain in the presence of said first bacteriophage panel,
   wherein the target bacterial strain growth conditions are the same or equivalent in steps (a) and (c);
   (d) rejecting said first bacteriophage panel as including antagonistic bacteriophages and as unsuitable for treating a bacterial infection when said first bacteriophage panel demonstrates less growth retardation than is demonstrated by any one of said three or more different bacteriophages by a same given time point;
   (e) providing a second bacteriophage panel, wherein said second bacteriophage panel is obtained by replacing at least one of the different bacteriophages from the first bacteriophage panel with at least one further different bacteriophage that retards growth of the target bacterial strain;
   (f) determining growth of the target bacterial strain in the presence of said second bacteriophage panel; and
   (g) accepting said second bacteriophage panel as excluding antagonistic bacteriophages and as suitable for treating the bacterial infection when:
      i. said second bacteriophage panel demonstrates growth retardation of the target bacterial strain that is more than or equal to the growth retardation demonstrated by any one bacteriophage of said first or second bacteriophage panels by the same given time point; and/or
      ii. said second bacteriophage panel demonstrates growth retardation of the target bacterial strain that is more than is demonstrated by said first bacteriophage panel by the same given time point; or (h) rejecting the second bacteriophage panel as including antagonistic bacteriophages and as unsuitable for treating the bacterial infection when:
  i. said second bacteriophage panel demonstrates growth retardation of the target bacterial strain that is less than is demonstrated by any one bacteriophage of said first or second bacteriophage panels by the same given time point; and/or
  ii. said second bacteriophage panel demonstrates growth retardation of the target bacterial strain that is equal to or less than is demonstrated by said first bacteriophage panel by the same given time point.

2. The method of claim 1, wherein growth of the target bacterial strain is determined in a bacterial liquid culture.

3. The method of claim 2, wherein growth of the target bacterial strain is determined in a bacterial liquid culture by measuring optical density of the liquid culture.

4. The method of claim 1, wherein the target bacterial strain is selected from: *Acinetobacter baumannii, Clostridium difficile, Escherichia coli, Klebsiella pneumonia, Pseudomonas aeruginosa, Stenotrophomonas maltophilia*, bacterial species causative of body odour, *Staphylococcus aureus*, and *Streptococcus mutans*.

5. The method of claim 1, wherein the time point is at least 2, 4, 8, 12, 16, 20, 24, 36 or 48 hours following addition of the bacteriophage panel to the target bacterial strain.

6. The method of claim 1, wherein growth of the target bacterial strain is the average growth of the target bacterial strain by a given time point.

* * * * *